United States Patent [19]

Umezawa et al.

[11] 4,091,202
[45] May 23, 1978

[54] N-METHANESULFONIC ACID DERIVATIVES OF 3',4'-DIDEOXYKANAMYCIN B

[75] Inventors: Hamao Umezawa; Sumio Umezawa; Shunzo Fukatsu; Shigeo Seki, all of Tokyo; Masao Murase, Kawasaki; Shuntaro Yasuda, Yokohama, all of Japan

[73] Assignee: Zaidan Hojin Biseibutsu Kagaku Kenkyu Kai, Tokyo, Japan

[21] Appl. No.: 723,832

[22] Filed: Sep. 16, 1976

[30] Foreign Application Priority Data

Sep. 25, 1975 Japan ............................. 50-114883

[51] Int. Cl.$^2$ .................. C07H 15/22; A61K 31/71
[52] U.S. Cl. ..................................... 536/10; 424/180
[58] Field of Search ........................... 536/10; 424/180

[56] References Cited

U.S. PATENT DOCUMENTS

| 2,599,950 | 6/1952 | Stansly et al. | 195/96 |
| 2,931,798 | 4/1960 | Umezawa et al. | 536/10 |
| 3,061,515 | 10/1962 | Fardig | 424/181 |
| 3,205,137 | 9/1965 | Lewis et al. | 424/181 |
| 3,268,508 | 8/1966 | Sugazawa et al. | 536/10 |
| 3,296,246 | 1/1967 | Ores et al. | 536/10 |
| 3,753,973 | 8/1973 | Umezawa et al. | 536/10 |
| 3,840,535 | 10/1974 | Kaplan et al. | 260/243 C |
| 4,001,208 | 1/1977 | Umezawa et al. | 536/10 |

FOREIGN PATENT DOCUMENTS

| 22,870 | 10/1963 | Japan | 536/10 |
| 874,028 | 8/1961 | United Kingdom | 536/10 |
| 896,774 | 5/1962 | United Kingdom | 536/10 |
| 902,992 | 8/1962 | United Kingdom | 536/10 |
| 933,702 | 8/1963 | United Kingdom | 536/10 |
| 957,433 | 5/1964 | United Kingdom | 536/10 |

*Primary Examiner*—Johnnie R. Brown
*Attorney, Agent, or Firm*—Herbert W. Taylor, Jr.

[57] ABSTRACT

As new semi-synthetic antibiotic derivative are provided N-methanesulfonic acid derivatives of 3',4'-dideoxykanamycin B which are less toxic than the parent antibiotic and have useful high antibacterial activity. They are produced by interacting 3',4'-dideoxykanamycin B, an aldehyde such as paraformaldehyde and sulfurous acid or an alkali metal sulfite reagent.

1 Claim, No Drawings

N-METHANESULFONIC ACID DERIVATIVES OF 3',4'-DIDEOXYKANAMYCIN B

BACKGROUND OF THE INVENTION

This invention relates to a less toxic derivative of 3',4'-dideoxykanamycin B which is a new compound valuable for use in therapeutic treatment of bacterial infections. This invention further relates to a method for the preparation of such less toxic derivative of 3',4'-dideoxykanamycin B.

It is known that 3',4'-dideoxykanamycin B is an important antibiotic substance which exhibits not only a wide antibacterial spectrum against a variety of pathogenic bacteria but also a high antibacterial activity against some kanamycin-resistant bacteria and *Pseudomonas aeruginosa* (see British Patent No. 1,349,302). Accordingly, if a new antibiotic derivative of 3',4'-dideoxykanamycin B which shows a lower toxicity than 3',4'-dideoxykanamycin B itself is provided, it will increase the applications of 3',4'-dideoxykanamycin B and make this antibiotic substance more valuable and important.

SUMMARY OF THE INVENTION

An object of this invention is to provide a new antibiotic derivative of 3',4'-dideoxykanamycin B which retains the useful antibacterial activity of 3',4'-dideoxykanamycin B but exhibits a lower toxicity than that of 3',4'-dideoxykanamycin B. The other object is to provide a method for the preparation of such new antibiotic derivative of 3',4'-dideoxykanamycin B. Another objects of this invention will be clear from the following descriptions.

As a result of extensive research, we, the present inventors, have now found that as new compounds, N-methanesulfonic acid derivatives of 3',4'-dideoxykanamycin B can be synthetized by interaction of 3',4'-dideoxykanamycin B, an aldehyde and sulfurous acid or an alkali metal hydrogen sulfite, and that these N-methanesulfonic acid derivatives are of lower toxicity than 3',4'-dideoxykanamycin B. Thus, 3',4'-dideoxykanamycin B contains five amino groups per molecule thereof and has a rational formula $C_{18}H_{27}O_8(NH_2)_5$. It has now been found that when 3',4'-dideoxykanamycin B, either in the form of free base or in the form of an acid-addition salt, is interacted with a molar proportion of an aldehyde of the formula:

RCHO wherein R is a hydrogen atom, an alkyl group, preferably an alkyl group of 1-4 carbon atoms, a substituted alkyl group, phenyl group or a substituted phenyl group, and a molar proportion of sulfurous acid or an alkali metal hydrogen sulfite which may be added concurrently or successively to the reaction system, there is produced a new N-methanesulfonic acid derivative according to the following reaction equation:

$$C_{18}H_{27}O_8(NH_2)_5 + n\ MHSO_3 + n\ RCHO$$

$$\longrightarrow C_{18}H_{27}O_8(NH_2)_{5-n}(\underset{\underset{R}{|}}{N}HCHSO_3M)_n$$

where R has the same meaning as defined above, n is an integer of 1 to 5, and M is a hydrogen atom or an alkai metal atom such as sodium and potassium. The number of the N-methanesulfonated amino groups present in the resulting N-methanesulfonic acid derivative of 3',4'-dideoxykanamycin B takes a value of 1, 2, 3, 4 or 5, depending upon the molar proportions of the aldehyde and the sulfurous acid or the sulfite compound employed for 1 molar proportion of 3',4'-dideoxykanamycin B.

DETAILS OF THE INVENTION

According to the first aspect of this invention, there is provided as a new compound a 3',4'-dideoxykanamycin B N-methanesulfonic acid derivative of the rational formula:

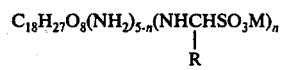

$$C_{18}H_{27}O_8(NH_2)_{5-n}(\underset{\underset{R}{|}}{N}HCHSO_3M)_n$$

wherein R is a hydrogen atom, an alkyl group, particularly an alkyl group of 1-4 carbon atoms, a substituted alkyl group, phenyl group or a substituted phenyl group, and M is a hydrogen atom or an alkali metal atom, and n is an integer of 1 to 5. When R denotes an alkyl group, it may preferably be a lower alkyl containing 1 to 4 carbon atoms, such as methyl, ethyl, n-butyl and n-propyl. R may also be a substituted alkyl group such as a lower alkyl bearing one or more methoxy or chloro substitutents thereon. Suitable examples of the substituted alkyl group include methoxymethyl, monochloromethyl and dichloromethyl. When R is a substituted phenyl group, it may be, for example, p-methoxyphenyl and o-hydroxyphenyl.

Particular examples of the new 3',4'-dideoxykanamycin B N-methanesulfonic acid derivative according to the invention are listed below:

(1) 3',4'-Dideoxykanamycin B-penta-N-methanesulfonic acid and its sodium salt of the following formula:

$$C_{18}H_{27}O_8(NHCH_2SO_3Na)_5$$

(2) 3',4'-Dideoxykanamycin B-tri-N-methanesulfonic acid and its sodium salt of the following formula:

$$C_{18}H_{27}O_8(NH_2)_2(NHCH_2SO_3Na)_3$$

(3) 3',4'-Dideoxykanamycin B-di-N-methanesulfonic acid and its sodium salt of the following formula:

$$C_{18}H_{27}O_8(NH_2)_3(NHCH_2SO_3Na)_2$$

(4) 3',4'-Dideoxykanamycin B-mono-N-methanesulfonic acid and its sodium salt of the following formula:

$$C_{18}H_{27}O_8(NH_2)_4(NHCH_2SO_3Na)$$

(5) 3',4'-Dideoxykanamycin B-di-N-methylmethanesulfonic acid and its sodium salt of the following formula:

$$C_{18}H_{27}O_8(NH_2)_3(\underset{\underset{CH_3}{|}}{N}HCHSO_3Na)_2$$

(6) 3',4'-Dideoxykanamycin B-penta-N-phenylmethane-sulfonic acid and its sodium salt of the following formula:

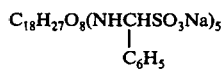

All of the compounds shown above are each a colorless powder having no definite melting point, which is readily soluble in water, sparingly soluble in methanol, ethanol and n-butanol but insoluble in benzene and ethylether.

The 3',4'-dideoxykanamycin B N-methanesulfonic acid derivatives of the invention exhibit high antibacterial activity against a wide variety of bacteria, similarly to the 3',4'-dideoxykanamycin B itself. Minimum inhibitory concentrations (mcg/ml) of the new compounds of the invention to various bacteria are estimated according to a standard serial dilution method using nutrient agar as the incubation medium, the incubation being made at 37° C for 41 hours. Minimum inhibitory concentrations of the parent antibiotic, 3',4'-dideoxykanamycin B (abbreviated as DKB) itself is estimated in the same manner, too, for the comparison purpose. The antibacterial spectra so obtained are shown in Table 1 below.

The N-methanesulfonic acid derivatives of 3',4'-dideoxykanamycin B according to the invention have a remarkably reduced acute toxicity, as compared to the 3',4'-dideoxykanamycin B itself, in spite of that they retain high antibacterial activity against various bacteria.

Acute toxicity of the various N-methanesulfonic acid derivatives of 3',4'-dideoxykanamycin B of the invention were determined by the following procedure: Thus, a test compound was dissolved in isotonic sodium chloride solution to give an aqueous solution containing the test compound at a concentration of 20% w/v, and varying volumes of the solution of the test compound so prepared were intravenously administered into a series of mouse groups each consisting of six mice (JCL-JCR strain, adult male, body weight 20 g ± 0.5 g) as the test animal, so that the test compound was given to each mouse at dosages of 3000 mg/kg, 3500 mg/kg, 4000 mg/kg, 4500 mg/kg and 6000 mg/kg. Acute toxicity of 3',4'-dideoxykanamycin B (free base) was also estimated in the same manner as above, for the comparison purpose. $LD_{50}$ values of the test compounds which have been estimated from the test results so obtained are tabulated in Table 2 below.

TABLE 1

Antibacterial spectra of N-methanesulfonic acid derivatives of 3',4'-dideoxykanamycin B (DKB) M.I.C.(mcg/ml)

| | DKB-penta-N-methane-sulfonic acid Na salt | DKB-tri-N-methane-sulfonic acid Na salt | DKB-di-N-methane-sulfonic acid Na salt | DKB-mono-N-methane-sulfonic acid Na salt | DKB-di-N methyl-methane-sulfonic acid Na salt | DKB-penta-N-phenyl-methane-sulfonic acid Na salt | DKB (comparative) |
|---|---|---|---|---|---|---|---|
| Staphylococcus aureus FDA 209P | <0.2 | <0.2 | <0.2 | <0.2 | <0.2 | <0.2 | <0.2 |
| Escherichia coli K-12 | 0.78 | 0.78 | 0.78 | 0.78 | 0.78 | 0.78 | 0.78 |
| Escherichia coli K-12 ML-1629 | 0.39 | 0.78 | 0.78 | 0.78 | 0.78 | 0.39 | 0.78 |
| Escherichia coli K-12 ML-1410 | 0.78 | 0.78 | 0.78 | 0.78 | 0.78 | 0.78 | 0.78 |
| Escherichia coli K-12 R81 | 0.78 | 0.78 | 0.78 | 0.78 | 0.78 | 0.78 | 0.78 |
| Escherichia coli K-12 MA290 R55 | 100 | 100 | 50 | 50 | 50 | 100 | 50 |
| Escherichia coli K-12 W677 | 0.78 | 0.78 | 0.78 | 0.78 | 0.78 | 0.78 | 0.78 |
| Escherichia coli K-12 JR66/W677 | 100 | 100 | 50 | 50 | 50 | 100 | 50 |
| Pseudomonas aeruginosa A3 | 0.78 | 0.78 | 0.78 | 0.78 | 0.78 | 0.78 | 0.78 |
| Pseudomonas aeruginosa No.12 | 3.12 | 3.12 | 1.56 | 1.56 | 1.56 | 3.12 | 1.56 |
| Pseudomonas aeruginosa GN315 | >100 | >100 | >100 | >100 | >100 | >100 | >100 |
| Proteus vulgaris OX19 | 0.39 | 0.39 | <0.2 | <0.2 | <0.2 | 0.39 | <0.2 |
| Klebsiella pneumoniae PCI602 | 0.39 | 0.39 | 0.39 | 0.39 | 0.39 | 0.39 | 0.39 |
| Bacillus subtilis PCI219 | 0.2 | 0.2 | <0.2 | <0.2 | <0.2 | 0.2 | <0.2 |
| Mycobacterium 607 | 0.78 | 0.78 | 0.39 | 0.39 | 0.39 | 0.78 | 0.39 |
| Shigella sonnei JS11746 | 1.56 | 1.56 | 0.78 | 0.78 | 0.78 | 1.56 | 0.78 |

Further, antibacterial potency of DKB-penta-N-methanesulfonic acid sodium salt and DKB-di-N-methane-sulfonic acid sodium salt of the invention is compared to that of DKB (free base) itself according to a cup-assay method using *Bacillus subtilis* as test organism, when it is observed that DKB-penta-N-methane-sulfonic acid sodium salt shows a potency of 400 units/mg, while DKB-di-N-methanesulfonic acid sodium salt shows a potency of 590 units/mg, assuming that DKB (free base) has a potency of 1000 units/mg.

TABLE 2

| Test Compounds | $LD_{50}$ value (mg/kg) |
|---|---|
| DKB-penta-N-methanesulfonic acid Na salt | >5000 |
| DKB-tri-N-methanesulfonic acid Na salt | >5000 |
| DKB-di-N-methanesulfonic acid Na salt | 4250 |
| DKB-mono-N-methanesulfonic acid Na salt | >1500 |
| DKB-di-N-methylmethane-sulfonic acid Na salt | >2000 |
| DKB-penta-N-phenylmethane-sulfonic acid Na salt | >5000 |
| DKB (free base) (comparative) | 100 – 120 |

From the results of Tables 1 and 2, it is seen that the new compounds of the invention have remarkably lower toxicity than the 3',4'-dideoxykanamycin B itself but retain usefully high antibacterial activity against various bacteria. In particular, 3',4'-dideoxykanamycin B-penta-N-methanesulfonic acid sodium salt and 3',4'-dideoxykanamycin B-di-N-methanesulfonic acid sodium salt are characteristically less toxic, such that their acute toxicity is reduced to about 1/40th of that of 3',4'-dideoxykanamycin B itself upon intravenous injection into mice, as will be seen from Table 2.

Moreover, it has been observed that even when the new compounds of the invention were injected intravenously into mice at a relatively higher dosage, they did not cause such adverse effect as convulsions, directly after the injection of the compounds.

The new compounds of the invention are effective in the treatment of systemic bacterial infections when administered intramuscularly in the dosage range of about 50 mg to about 500 mg per day in divided doses three or four times a day. Generally the new compounds may be administered orally, intraperitoneally, intravenously or intramuscularly using any pharmaceutical form known to the art for such administration and in a similar manner to kanamycins. Examples of pharmaceutical forms for oral administration are powders, capsules, tablets, syrup and the like.

In order to estimate $ED_{50}$ values of DKB-penta-N-methanesulfonic acid sodium salt and DKB-di-N-methane-sulfonic acid sodium salt of this invention for therapeutic treatment of bacterial infection in mice, tests were made in the following way:- Thus, to several groups each consisting of 10 mice of ICR-strain (4-week-aged male, average body weight 20 g.) was inoculated Staphylococcus aureus Smith S-424 at an inoculum of $27.8 \times 10^4$ cells per mouse by intraperitoneally injecting a suspension of $27.8 \times 10^4$ cells of the bacterium in 0.5 cc. of sterile, isotonic sodium chloride solution. Said inoculum is corresponding to a 860-fold quantity of the $LD_{50}$ dosage of S.aureus Smith S-424. A solution of the test compound in sterile, isotonic sodium chloride solution was intramuscularly injected into the infected mice once immediately after the inoculation of the bacterium at dosages of 0.1 mg, 0.05 mg, 0.025 mg, 0.0125 mg and 0.0063 mg of the test compound per mouse. From the test results as obtained, it is estimated that DKB-penta-N-methanesulfonic acid sodium salt exhibits an $ED_{50}$ value of 1.9 mg/kg and that DKB-di-N-methanesulfonic acid sodium salt exhibits an $ED_{50}$ value of 1.15 mg/kg for the above therapeutic tests. DKB itself was tested in the same manner as above for the comparison purpose, and it is estimated that DKB exhibits an $ED_{50}$ value of 1.15 mg/kg.

For the preparation of the new compounds of the invention, 3',4'-dideoxykanamycin B, either in the free base form or in the form of an acid-addition salt thereof, an aldehyde of the formula RCHO as defined hereinbefore and sulfurous acid or an alkali metal hydrogen sulfite, are interacted with each other, as stated before. The aldehyde and the sulfurous acid or alkali metal sulfite may be reacted concurrently with 3',4'-dideoxykanamycin B, or alternatively either one of the aldehyde reagent and the sulfurous acid or alkali metal sulfite reagent may be reacted at first with 3',4'-dideoxykanamycin B prior to the addition of the remaining reagent.

According to a second aspect of the present invention, therefore, there is provided a method for the preparation of a 3',4'-dideoxykanamycin B N-methanesulfonic acid derivative of the rational formula:

$$C_{18}H_{27}O_8(NH_2)_{5-n}(NHCHSO_3M)_n$$
$$|$$
$$R$$

wherein R is a hydrogen atom, an alkyl group, a substituted alkyl group, phenyl group or a substituted phenyl group, and M is a hydrogen atom or an alkali metal atom, and n is an integer of 1, 2, 3, 4 or 5, which comprises conducting interaction between 3',4'-dideoxykanamycin B free base or an acid-addition salt thereof, sulfurous acid or an alkali metal hydrogen sulfite and an aldehyde of the formula:

RCHO wherein R is as defined above.

In the method of the invention, the starting material, 3',4'-dideoxykanamycin B may be employed either in the form of free base or in the form of an acid-addition salt thereof, which may conveniently be in the form of the sulfate or hydrochloride. When sulfurous acid is used as one of the reagents, it may conveniently be used in the form of gaseous sulfur dioxide. However, it is feasible, of course, to employ aqueous sulfurous acid. Instead of the sulfurous acid reagent, an alkali metal hydrogen sulfite may be used as an equivalent agent. Sodium hydrogen sulfite, potassium hydrogen sulfite and lithium hydrogen sulfite are suitable as the alkali metal hydrogen sulfite for the purpose of the invention. Suitable examples of the aldehyde reagent RCHO available for the invention include paraformaldehyde, acetaldehyde, methoxyacetaldehyde, monochloroacetaldehyde, dichloroacetaldehyde, glyoxal, propionaldehyde, n-butylaldehyde, benzaldehyde, p-methoxybenzaldehyde and salicylaldehyde.

When either one of the aldehyde reagent and the sulfurous acid or alkali metal hydrogen sulfite reagent is reacted at first with 3',4'-dideoxykanamycin B in the method of the invention, it is feasible to carry out the method in such a manner that the aldehyde reagent is reacted at first with 3',4'-dideoxykanamycin B to produce the corresponding Schiff's base so formed, this Schiff's base is isolated and then reacted with the sulfurous acid or alkali metal hydrogen sulfite reagent to yield the desired 3',4'-dideoxykanamycin B N-methanesulfonic acid derivative as the final product. Alternatively, it is possible to conduct the method in such a manner that the sulfurous acid or sulfite reagent is at first reacted with 3',4'-dideoxykanamycin B to convert the latter into the form of an acid-addition salt with sulfurous acid, which is subsequently reacted with the aldehyde reagent to yield the desired N-methanesulfonic acid derivative as the final product.

The molar proportions of the aldehyde reagent and the sulfurous acid or sulfite reagent to be interacted with 3',4'-dideoxykanamycin B may vary from 1 molar to 5 molar proportions for 1 molar proportion of 3',4'-dideoxykanamycin B. The N-methanesulfonic acid derivatives obtained as the final product by the method of the invention contain the methanesulfonic acid component at different contents depending on the molar proportions of the aldehyde reagent and the sulfurous acid or sulfite reagent employed. For instance, when the interaction is conducted using 1 molar proportion of 3',4'-dideoxykanamycin B, 5 molar proportions of paraformaldehyde and 5 molar proportion of sodium hydrogen sulfite, there is produced 3',4'-dideoxykanamycin B-penta-N-methanesulfonic acid sodium salt. While 3',4'-dideoxykanamycin B-di-N-methanesulfonic acid sodium salt is produced when the interaction is made using 1 molar proportion of 3',4'-dideoxykanamycin B, 2 molar proportions of paraformaldehyde and 2 molar proportions of sodium hydrogen sulfite. Generally, the method may be carried out at ambient temperature or at an elevated temperature for a reaction time of about 6 hours to 20 hours using water as the reaction medium, and the desired interaction product may be precipitated by addition of methanol or ethanol to the aqueous reaction solution. The preparation of 3',4'-dideoxykanamycin B-penta-N-methanesulfonic acid sodium salt may be achieved conveniently by dissolving 1 molar proportion of 3',4'-dideoxykanamycin B (free base) in water, admixing the resulting aqueous solution with 5 molar proportions of paraformaldehyde and 5 molar proportions of sodium hydrogen sulfite, shaking the reaction mixture in a sealed reaction vessel at ambient temperature for about 16 hours, and after the completed reaction, adding a water-miscible organic liquid in which the desired interaction product is insoluble, such as methanol and ethanol, to the reaction solution to precipitate the desired product as a colorless deposit. The colorless precipitate is filtered out, washed with methanol or ethanol and then dried to afford the desired 3',4'-dideoxykanamycin B-penta-N-methanesulfonic acid sodium salt in a yield of 90% or more.

That the new derivatives of 3',4'-dideoxykanamycin B as produced by the method of the invention have the molecular structure corresponding to that of an N-methanesulfonic acid derivative has been confirmed from the infra-red absorption spectrophotometry as well as from the experiments showing that they liberate formaldehyde when hydrolyzed with diluted hydrochloric acid.

As stated before, the new compounds of the invention are effective in treatment of systemic bacterial infections. According to a third aspect of the invention, therefore, there is provided an antibacterial pharmaceutical composition for treating bacterial infections in a living animal, comprising an antibacterially effective amount of a 3',4'-dideoxykanamycin B N-methanesulfonic acid derivative of the rational formula:

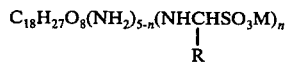

wherein R is a hydrogen atom, an alkyl group, a substituted alkyl group, phenyl group, or a substituted phenyl group, and M is a hydrogen atom or an alkali metal atom, and $n$ is an integer of 1, 2, 3, 4 or 5, in combination with a pharmaceutically acceptable carrier therefor.

DESCRIPTION OF THE PREFERRED EMBODIMENTS

The invention is now illustrated with reference to the following Examples which are in no way limitative for the invention.

EXAMPLE 1

3',4'-Dideoxykanamycin B free base (4.52 g; 0.01 mol.) was dissolved in distilled water (7 ml), and the resultant aqueous solution was admixed with sodium hydrogen sulfite (5.2 g; 0.05 mol.) and paraformaldehyde (1.5 g; 0.05 mol.). The admixture so obtained was shaken overnight in a sealed flask at ambient temperature for the interaction. After this, the reaction solution was filtered on a glass-filter and the filtrate was poured into methanol (100 ml) under agitation to deposit a colorless precipitate. This precipitate was collected by filtration and dried at 50° C to a constant weight, affording 10.0 g. of 3',4'-dideoxykanamycin B-penta-N-methanesulfonic acid sodium salt as a colorless powder having no definite melting point. Yield 99%, $[\alpha]_D^{20}$ + 49° (c 1.1 water).

Elemental analysis
Found: C 26.32, H 4.33, N 6.36, S 15.86%; Calcd. for $C_{18}H_{27}O_8(NHCH_2SO_3Na)_5$: C 26.77, H 4.07, N 6.79, S 15.52%.

Infrared absorption spectrum of this product was determined to show that absorption peaks occur at about 3450 cm$^{-1}$ (attributable to OH and NH), at 1635 cm$^{-1}$ (characteristic to the methanesulfonate) and at 1190 cm$^{-1}$ and 1035 cm$^{-1}$ (characteristic to the methanesulfonate). These data support that the product of this Example has the molecular structure of the N-methanesulfonic acid derivative.

The 3',4'-dideoxykanamycin B derivative (0.2 g) obtained as the final product of this Example was dissolved in a mixture of 2N hydrochloric acid (3 ml) and water (5 ml), and the solution so obtained was heated on a boiling water bath for 15 minutes. After the reaction solution was allowed to cool, it was neutralized by addition of aqueous 1N sodium hydroxide. The neutralized solution was then admixed with a solution of dimedone (200 mg) in a mixed solvent of water (0.5 ml) and methanol (1 ml), and the admixture was heated at 80° C for 60 minutes and then left to cool, depositing colorless needles of formaldehydemethone, m.p. 190° C. When the colorless crystalline product was subjected to a mixed melting point test with an authentic sample of formaldehydemethone, no depression in the melting point was observed. This result reveals that the 3',4'-dideoxykanamycin B derivative obtained in this Example is a methanesulfonic acid derivative.

EXAMPLE 2

3',4'-Dideoxykanamycin B free base (4.52 g; 0.01 mol.) was taken up into 10 ml. of distilled water, and into the resulting aqueous solution was passed a dry gaseous sulfur dioxide until the sulfur dioxide (0.64 g; 0.01 mol.) has been absorbed by said aqueous solution. To this solution was further added paraformaldehyde (0.3 g; 0.01 mol.) in the powdery form. The admixture was shaken overnight in a sealed flask at ambient temperature to effect the interaction. The clear reaction solution so obtained was poured into ethanol (100 ml) under agitation, and a colorless precipitate deposited was collected by filtration and then dried 3',4'-Dideoxykanamycin B-mono-N-methanesulfonic acid (5.19 g) was obtained as a colorless powder. Yield 95% $[\alpha]_D^{20}$ + 112° (c 1, H$_2$O)

Elemental analysis
Found: S 5.67% Calcd. for $C_{18}H_{27}O_8(NH_2)_4(NHCH_2SO_3H)$: S 5.87%.

EXAMPLE 3

The process of Example 1 was repeated using 2.26 g. (5 millimol.) of 3',4'-dideoxykanamycin B free base, 5 ml. of distilled water, 1.56 g. (15 milimol.) of sodium hydrogen sulfite and 0.45 g. (15 milimol.) of paraformaldehyde. 3',4'-Dideoxykanamycin B-tri-N-methanesulfonic acid sodium salt (3.88 g.) was obtained as a colorless powder. Yield 97% $[\alpha]_D^{20} + 76°$ (c 1, $H_2O$)

Elemental analysis

Found: S 12.18% Calcd. for $C_{18}H_{27}O_8(NH_2)_2(NHCH_2SO_3Na)_3$: S 12.02%.

EXAMPLE 4

Dry gaseous sulfur dioxide was passed into a solution of 4.51 g. (0.01 mol.) of 3',4'-dideoxykanamycin B free base in 8 ml. of distilled water, until 1.28 g. (0.02 mol.) of the sulfur dioxide had been absorbed by said solution. To said solution was added 1.26 g. of a solution containing 70% by weight of acetaldehyde in water, under agitation. The admixture was allowed to stand for 24 hours at ambient temperature to effect the interaction, and the reaction solution was then processed in the same manner as described in Example 1. The colorless precipitate collected was dried at 50° C to a constant weight. 3',4'-dideoxykanamycin B-di-N-methylmethanesulfonic acid (6.01 g.) was obtained as a colorless powder. Yield 90%. $[\alpha]_D^{20} + 90°$ (c 1, $H_2O$)

Elemental analysis

Found: S 9.32% Calcd. for

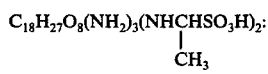

S 9.60%.

EXAMPLE 5

To a solution of 4.51 g. (0.01 mol.) of 3',4'-dideoxykanamycin B free base in 10 ml. of distilled water were added sodium hydrogen sulfite (5.2 g; 0.05 mol.) and benzaldehyde (5.3 g; 0.05 mol.) under stirring. The admixture was allowed to stand at ambient temperature for 24 hours to effect the interaction. The reaction solution so obtained was subsequently processed in the same manner as in Example 1. The colorless precipitate collected was dried at 50° C to a constant weight. 3',4'-Dideoxykanamycin B-penta-N-phenylmethanesulfonic acid sodium salt was obtained as a colorless powder. $[\alpha]_D^{20} + 42°$ (c 1.0, $H_2O$) Yield 13.0 g. (92%).

Elemental analysis

Found: S 11.02%; Calcd. for

S 11.30%

EXAMPLE 6

The process of Example 1 was repeated using 4.52 g. (0.01 mol.) of 3'4'-dideoxykanamycin B free base, 2.1 g.(ca. 0.02 mol.) of sodium hydrogen sulfite and 0.6 g.(0.02 mol.) of paraformaldehyde. 3',4'-Dideoxykanamycin B-di-N-methanesulfonic acid sodium salt was obtained as a colorless powder. Yield 6.80 g. (99%). $[\alpha]_D^{20} + 95°$ (c 1.0, $H_2O$)

Elemental analysis

Found: S 9.05%;
Calcd. for $C_{18}H_{27}O_8(NH_2)_3(NHCH_2SO_3Na)_2$: S 9.35%.

What we claim is:

1. A compound which is selected from
   3',4'-dideoxykanamycin B-penta-N-methanesulfonic acid;
   3',4'-dideoxykanamycin B-tri-N-methanesulfonic acid;
   3',4'-dideoxykanamycin B-di-N-methanesulfonic acid;
   3',4'-dideoxykanamycin B-mono-N-methanesulfonic acid;
   3',4'-dideoxykanamycin B-di-N-methylmethanesulfonic acid;
   3',4'-dideoxykanamycin B-penta-N-phenylmethanesulfonic acid
   and alkali metal salts of these acids.